(12) United States Patent
Suzuki

(10) Patent No.: US 9,326,454 B2
(45) Date of Patent: May 3, 2016

(54) METHOD FOR CULTIVATING PLANT

(71) Applicant: SHOWA DENKO K.K., Minato-ku, Tokyo (JP)

(72) Inventor: Hiroshi Suzuki, Minato-ku (JP)

(73) Assignee: SHOWA DENKO K.K., Tokyo (JP)

( * ) Notice: Subject to any disclaimer, the term of this patent is extended or adjusted under 35 U.S.C. 154(b) by 188 days.

(21) Appl. No.: 14/171,014

(22) Filed: Feb. 3, 2014

(65) Prior Publication Data

US 2014/0215911 A1     Aug. 7, 2014

(30) Foreign Application Priority Data

Feb. 4, 2013  (JP) ................................. 2013-019722

(51) Int. Cl.
*A01G 7/04*     (2006.01)
*A01H 3/02*     (2006.01)

(52) U.S. Cl.
CPC . *A01G 7/045* (2013.01); *A01H 3/02* (2013.01)

(58) Field of Classification Search
CPC ............ A01G 7/00; A01G 7/04; A01G 7/045
USPC ............... 47/1.01 R, 62 R, 62 N, 1.3, 58.1 R, 47/58.1 LS, 58.1 SE, DIG. 6, 1.4
IPC ................................................. A01G 7/00, 7/04
See application file for complete search history.

(56) References Cited

U.S. PATENT DOCUMENTS

| 3,673,733 | A | * | 7/1972 | Allen ..................... A01G 9/246 165/47 |
| 7,895,790 | B2 | * | 3/2011 | Lin ........................ C12M 21/02 435/289.1 |
| 9,137,874 | B2 | * | 9/2015 | Maxik ..................... H05B 37/02 |
| 2011/0115385 | A1 | * | 5/2011 | Waumans ............... A01G 7/045 315/152 |
| 2012/0218750 | A1 | * | 8/2012 | Klase ..................... A01G 7/045 362/231 |

(Continued)

FOREIGN PATENT DOCUMENTS

| JP | 6-276858 A | 10/1994 |
| JP | 8-103167 A | 4/1996 |
| JP | 2005-52105 A | 3/2005 |

(Continued)

OTHER PUBLICATIONS

Japanese Office Action dated Oct. 7, 2014 issued in corresponding application No. 2014-018642.
European Search Report issued in application No. 14153601.1-1656 dated Jun. 14, 2014.
European Search Report issued in application No. 14153601.1-1656 dated Jun. 20, 2014.

*Primary Examiner* — Lisa Tsang
(74) *Attorney, Agent, or Firm* — Sughrue Mion, PLLC

(57) ABSTRACT

A plant-cultivating method is provided which comprises a red light irradiation step (A) and a blue light irradiation step (B), wherein the step (A) and the step (B) are independently carried out for a predetermined period of time under cultivation conditions such that amounts of nitrogen, phosphorus and potassium as fertilizer ingredients as used at the step (B) are smaller than amounts of nitrogen, phosphorus and potassium as fertilizer ingredients, respectively, as used at the step (A). Preferably, fertilizer ingredients are applied in amounts such that a growth medium at the step (B) contains 10-15 me/L of nitrogen, 1-4 me/L of phosphorus and 2-6 me/L of potassium, and a growth medium at the step (A) contains 15-20 me/L of nitrogen, 3-6 me/L of phosphorus and 6-9 me/L of potassium.

10 Claims, 1 Drawing Sheet

(56) References Cited

U.S. PATENT DOCUMENTS

2014/0170733 A1\* 6/2014 Shigyo .................. A01G 33/00
 435/257.3
2015/0223402 A1\* 8/2015 Krijn ...................... A01G 7/045
 47/58.1 LS

FOREIGN PATENT DOCUMENTS

| JP | 2006-067948 A | 3/2006 |
| JP | 2008-142005 A | 6/2008 |
| JP | 2012-179009 A | 9/2012 |

\* cited by examiner

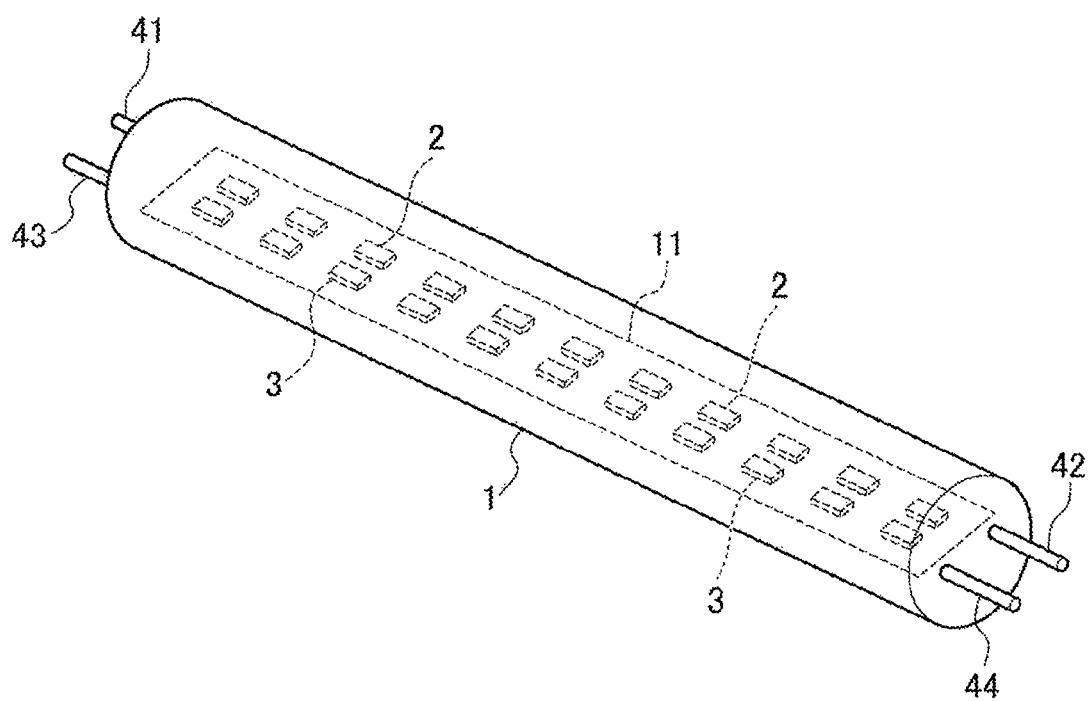

METHOD FOR CULTIVATING PLANT

BACKGROUND OF THE INVENTION (1) Field of the Invention

This invention relates to a method for cultivating a plant. More particularly it relates to a method for cultivating a plant while the plant is irradiated with an artificial light using a light-emitting lamp for plant cultivation whereby growth of the plant is promoted.

(2) Description of Related Art

Light-emitting technology has heretofore been adopted for growing seedlings or promoting growth of plants whereby a cultivation period of plants can be shortened and frequency of harvesting in the same farm can be increased. Plants can be grown to a large size within a predetermined period of time, and the crop yield can be enhanced.

As a plant cultivation technique utilizing artificial light irradiation, an illumination lamp facility for irradiating a plant alternately with green light and white light has been proposed, for example, in patent document 1. In this illumination lamp facility, plants are irradiated alternately with green light having a wavelength of 500 to 570 nm and white light having a wavelength of 300 to 800 nm whereby simulated day and night are created. Consequently the sugar translocation within plant bodies is smoothly effected and growth of plants is enhanced.

Another proposal has been proposed in patent document 2, which comprises an illumination lamp facility equipped with a light emitting diode (LED) for irradiating plants alternately or concurrently with blue light having a wavelength of 400-480 nm and red light having a wavelength of 620-700 nm to supply light energy for cultivation, growth, and tissue cultivation of plants. This illumination lamp facility is characterized as irradiating plants selectively with light having a wavelength corresponding to the light absorption peak of chlorophyll, i.e., in the vicinity of 450 nm and the vicinity of 660 nm whereby the plants are cultivated with an enhanced energy efficiency.

It is stipulated in patent document 2 that blue light and red light may be irradiated either concurrently or alternately (see patent document 2, claim 1). More specifically it is described in this patent document that single radiation of blue light, single radiation of red light and concurrent radiation of blue light and red light are compared with each other, and it was verified that the concurrent radiation of blue light and red light exhibited an enhanced effect on healthy growth of plants, which is similar to the growth achieved by sun light radiation, whereas the single radiation of blue light or red light brings about unhealthy growth such as spindly growth of plants (see patent document 2, paragraph [0011]). It is further described in patent document 2 that blue light and red light are alternately radiated by blinking by means of a blinking pattern at a high frequency of several megahertz or more (see patent document 2, paragraph [0006]).

However, patent document 2 is silent on a method of alternately conducting a blue light irradiation step and a red light irradiation step, and thus, growth promoting effects achieved by the alternate light irradiation method are not verified.

PRIOR ART DOCUMENTS

Patent Documents
Patent document 1: JP 1994-276858A
Patent document 2: JP 1996-103167A To enhance the productivity in plant cultivation, a plant cultivation method utilizing artificial light irradiation, which is simple and easy, and exhibits enhanced energy efficiency and excellent growth promotion effect, is eagerly desired.

BRIEF SUMMARY OF THE INVENTION

A primary object of the present invention is to provide an improved method of cultivating a plant using an artificial light-irradiating facility, whereby high value-added and highly nutritious plants can be produced with improved growth promotion effect.

The present inventors made extensive research for providing an improved method for cultivating a plant using an artificial light-irradiating lamp facility with enhanced growth promotion effect, and have found that an enhanced growth promotion effect is achieved by a plant-cultivation method comprising a step (A) of irradiating a plant with a red light and a step (B) of irradiating the plant with a blue light, wherein the two steps (A) and (B) are independently carried out for a predetermined period of time, and further found that the growth promotion effect varies depending upon the cultivation conditions, especially the fertilization conditions. An excellent growth promotion effect has been obtained by applying fertilizers containing smaller amounts of fertilizer ingredients at the blue light irradiation step (B) than the amounts of fertilizer ingredients in the fertilizers applied at the red light irradiation step (A). Based on these findings, the present invention has been completed.

In accordance with the present invention, there are provided the following plant-cultivating methods.

(1). A method of cultivating a plant comprising a step (A) of irradiating a plant with a red light and a step (B) of irradiating a plant with a blue light, wherein the red light irradiation step (A) and the blue light irradiation step (B) are independently carried out for a predetermined period of time under cultivation conditions such that amounts of nitrogen, phosphorus and potassium as fertilizer ingredients applied at the blue light irradiation step (B) are smaller than amounts of nitrogen, phosphorus and potassium as fertilizer ingredients, respectively, applied at the red light irradiation step (A).

(2). The method of cultivating a plant as mentioned above in (1), wherein the fertilizer ingredients are applied in amounts such that a growth medium at the blue light irradiation step (B) contains 10 to 15 me/L of nitrogen, 1 to 4 me/L of phosphorus and 2 to 6 me/L of potassium, and a growth medium at the red light irradiation step (A) contains 15 to 20 me/L of nitrogen, 3 to 6 me/L of phosphorus and 6 to 9 me/L of potassium.

(3). The method of cultivating a plant as mentioned above in (1), wherein the fertilizer ingredients are applied in the form of a nutritious liquid at the blue light irradiation step (B) and the red light irradiation step (A), and the nutritious liquid applied at the blue light irradiation step (B) has a pH value smaller than a pH value of the nutritious liquid applied at the red light irradiation step (A).

(4). The method of cultivating a plant as mentioned above in (1), wherein the fertilizer ingredients are applied in the form of a nutritious liquid at the blue light irradiation step (B) and the red light irradiation step (A), and the nutritious liquid applied at the blue light irradiation step (B) has a pH value in the range of 4 to 5, and the nutritious liquid applied at the red light irradiation step (A) has a pH value in the range of 5 to 6.5.

(5). The method of cultivating a plant as mentioned above in (1), wherein the fertilizer ingredients are applied in the form of a nutritious liquid at the blue light irradiation step (B) and at the red light irradiation step (A), and a temperature of the nutritious liquid applied at the blue light irradiation step (B) is lower than a temperature of the nutritious liquid applied at the red light irradiation step (A).

(6). The method of cultivating a plant as mentioned above in (5), wherein the temperature of the nutritious liquid applied at the blue light irradiation step (B) is in the range of 10° C. to 18° C. and the temperature of the nutritious liquid applied at the red light irradiation step (A) is in the range of 15° C. to 25° C.

(7). The method of cultivating a plan as mentioned above in (1), wherein the plant is selected from algae, phytoplankton and euglena.

(8). The method of cultivating a plant as mentioned above in (1), wherein the red light-irradiation step (A) and the blue light irradiation step (B) are alternately and repeatedly carried out over a period of at least one hour for each irradiation time.

(9). The method of cultivating a plant as mentioned above in (1), wherein the red light irradiation step (A) and the blue light irradiation step (B) are carried out using an illumination lamp facility having red light emitting elements and blue light emitting elements, both of which are capable of being independently operated, and the red light emitting elements and the blue light emitting elements exhibit a light emission intensity ratio of red light to blue light of at least 1:1 as expressed by a ratio of photosynthetic photon flux density of red light to blue light.

(10). The method of cultivating a plant as mentioned above in (1), wherein the red light irradiation step (A) and the blue light irradiation step (B) are carried out using an illumination lamp facility having red light emitting elements and blue light emitting elements, both of which are capable of being independently operated, and the red light emitting elements and the blue light emitting elements exhibit a light emission intensity ratio of red light to blue light in the range of 2:1 to 9:1 as expressed by a ratio of photosynthetic photon flux density of red light to blue light.

By the term "plant(s)" as used in this specification, we mean plants in a broad sense which include leaf plants, fruit plants, grains and algae. The plant cultivation method according to the present invention exhibits especially marked growth promotion effect for phytoplankton such as algae, and mosses and euglena.

EFFECT OF THE INVENTION

By independently carrying out the red light irradiation step (A) and the blue light irradiation step (B), and further by using fertilizers containing relatively small amounts of nitrogen, phosphorus and potassium at the blue light irradiation step (B), and using fertilizers containing relatively large amounts of nitrogen, phosphorus and potassium at the red light irradiation step (A) according to the present invention, high value-added and highly nutritious plants can be produced with improved growth promotion effect.

BRIEF DESCRIPTION OF THE DRAWINGS

FIG. 1 is a perspective view of an example of an illumination lamp having red light emitting elements and blue light emitting elements as used in the plant-cultivation method of the present invention.

DETAILED DESCRIPTION OF THE INVENTION

Preferred modes for practicing the invention will be described with reference to the accompanying drawings. The described modes by no means limit the scope of the invention.

The plant cultivation method of the present invention is characterized by comprising a step (A) of irradiating the plant with a red light and a step (B) of irradiating the plant with a blue light, wherein the red light irradiation step (A) and the blue light irradiation step (B) are independently carried out for a predetermined period of time under cultivation conditions such that amounts of nitrogen, phosphorus and potassium as fertilizer ingredients applied at the blue light irradiation step (B) are smaller than amounts of nitrogen, phosphorus and potassium as fertilizer ingredients, respectively, applied at the red light irradiation step (A).

When red light and blue light are irradiated on a plant, the light absorption curve of chlorophyll has different peaks attributed to the red light and the blue light. Thus the red light and the blue light exhibit different functions. The red light is concerned with activation of phytochrome, and the blue light is concerned with activation of phototropin and cryptochrome. The present inventors have investigated the difference between the functions of red light and blue light in the growth of plants, and found that red light tends to enlarge the area of plant leaves, and blue light tends to be concerned with morphogenesis of plants.

The mechanism on which red light and blue light have the different functions is not clear, but it is presumed that red light and blue light exhibit different chemical reactions with regard to the photosynthesis reaction, and amounts of primary nutrients, i.e., nitrogen, phosphorus and potassium in a fertilizer used is also closely concerned with the photosynthesis reaction.

More specifically the present inventors made researches on the fertilization conditions, especially the contents of nutrients in fertilizers used at the red light irradiation step and the blue light irradiation step, and found that the growth promotion effect of plants, the contents of nutrients and minerals in plants can be more enhanced by using fertilizers at the blue light irradiation step (B), which contain nitrogen, phosphorus and potassium in amounts smaller than amounts of nitrogen, phosphorus and potassium, respectively, contained in fertilizers used at the red light irradiation step (A).

Three primary fertilizer ingredients (nutrients), i.e., nitrogen, phosphorus and potassium, are essential for the growth of plants. Nitrogen takes part in proliferation and growth of cells, and thus, indispensable for growth of plants. Phosphorus is an ingredient of nucleic acid in plants, and has a role of promoting growth of plants. Potassium has a role of promoting growth of plant roots. Other nutrients such as minerals including, for example, calcium, magnesium and iron are preferably contained in a liquid fertilizer.

In the plant cultivation method of the present invention, the amounts of the primary fertilizer ingredients, i.e., nitrogen, phosphorus and potassium, applied at the red light irradiation step (A) are larger than the amounts of nitrogen, phosphorus and potassium applied at the blue light irradiation step (B). However, it has been found that, in the case when an amount of at least one fertilizer ingredient among nitrogen, phosphorus and potassium applied at the red light irradiation step (A) is larger than an amount of the corresponding fertilizer ingredient among nitrogen, phosphorus and potassium applied at the blue light irradiation step (B), a good growth promotion effect can be attained. However, a better growth promotion effect is attained in the case when amounts of all of nitrogen, phosphorus and potassium applied at the red light irradiation step (A) are larger than amounts of the corresponding fertilizer ingredients among nitrogen, phosphorus and potassium applied at the blue light irradiation step (B).

The fertilizer ingredients are applied preferably in amounts such that a growth medium at the blue light irradiation step (B) contains 10 to 15 me/L of nitrogen, 1 to 4 me/L of phosphorus and 2 to 6 me/L of potassium, and a growth medium at the red light irradiation step (A) contains 15 to 20 me/L of nitrogen, 3 to 6 me/L of phosphorus and 6 to 9 me/L of potassium.

The growth medium is not particularly limited, and conventional natural and artificial growth mediums can be used. An aqueous growth medium is preferably used, and an aqueous nutritious liquid containing fertilizer ingredients can be used as a growth medium.

As specific examples of the fertilizers as used in the present invention, there can be mentioned nitrogen fertilizers such as ammonium sulfate, ammonium chloride, ammonium nitrate, urea, nitrogenous lime, potassium nitrate, calcium nitrate and sodium nitrate; phosphate fertilizers such as superphosphate of lime and fused magnesium phosphate; potassium fertilizers such as potassium chloride and potassium sulfate.

In the plant-cultivation method of the present invention, the red light irradiation step (A) and the blue light irradiation step (B) are independently carried out for a predetermined period of time. By carrying out separately the red light irradiation and the blue light irradiation, the desired plant growth promoting effect can be attained. If the red light irradiation and the blue light irradiation are concurrently carried out, the photosynthesis processes by the red light irradiation and the blue light irradiation interfere with each other and do not proceed effectively.

In the plant-cultivation method according to the present invention, it is preferable that the fertilizers used at both of the blue light irradiation step (B) and the red light irradiation step (A) are in the form of a nutritious liquid, and, the nutritious liquid applied at the blue red light irradiation step (B) have a pH value smaller than a pH value of the nutritious liquid applied at the red light irradiation step (A).

More preferably the difference between the pH value of the nutritious liquid applied at the blue light irradiation step (B) and the pH value of the nutritious liquid applied at the red light irradiation step (A) is in the range of 1 to 2.

It is preferable for further enhancing the plant growth promotion effect that the fertilizer ingredients applied at both of the blue light irradiation step (B) and the red light irradiation step (A) are in the form of a nutritious liquid, and, a temperature of the nutritious liquid applied at the blue light irradiation step (B) is lower than a temperature of the nutritious liquid applied at the red light irradiation step (A).

More specifically, the temperature of the nutritious liquid applied at the blue light irradiation step (B) is preferably in the range of 10° C. to 18° C. and the temperature of the nutritious liquid applied at the red light irradiation step (A) is in the range of 15° C. to 25° C. The difference between the temperature of the nutritious liquid applied at the blue light irradiation step (B) and the temperature of the nutritious liquid applied at the red light irradiation step (A) is in the range of 5° C. and 10° C.

Illumination Lamp for Plant Cultivation

In the plant-cultivation method of the present invention, an illumination lamp facility for plant cultivation having red light emitting elements and blue light emitting elements, both of which are capable of being independently operated, is used for independently (preferably, alternately and repeatedly) carrying out the red light irradiation step (A) and the blue light irradiation step (B) for a predetermined period of time.

FIG. 1 is a perspective view of a preferable example of an illumination lamp for plant cultivation which has red light emitting elements and blue light emitting elements. This illumination lamp 1 has a light irradiation part 11 having a rectangular shape in the planar view, and further has a control part (not shown) for controlling the light irradiation part 11.

As illustrated in FIG. 1, the light irradiation part 11 is provided with plural red light emitting elements 2 and plural blue light emitting elements 3. In the plant cultivation lamp 1, as specifically illustrated in FIG. 1, the number of red light emitting elements 2 and the number of blue light emitting elements 3 are the same.

Plural red light emitting elements 2 are arranged with equal intervals along a straight line extending in the length direction of the light irradiation part 11, and plural blue light emitting elements 3 are also arranged in a similar manner. The straight line of red light emitting elements 2 and the straight line of blue light emitting elements 3 are substantially parallel to each other.

The number of red light emitting elements 2 and the number of blue light emitting elements 3 may be the same or different in the illumination lamp 1, although the number of red light emitting elements 2 to the number of blue light emitting elements 3 in the lamp illustrated in FIG. 1 is 2:1.

The rate of plant growth sometimes varies depending upon the light emission intensity ratio of red light and blue light. For example, some plants exhibit enhanced rate of growth when the red light emission intensity is larger than the blue light emission intensity. For these plants, it is preferable to use a plant cultivating illumination lamp 1 having a light emitting part provided with a larger number of red light emitting elements 2 than blue light emitting elements 3. By using the lamp 1 provided with a larger number of red light emitting elements 2 than blue light emitting elements 3, the light emission intensity of red light can be easily made larger than that of blue light.

For many plants, the light emission intensity of red light is preferably larger than that of blue light. Practically, for these plants, the light emission intensity ratio of red light to blue light (i.e., a ratio of the total emission intensity of red light to the total emission intensity of blue light) is preferably at least 1:1, more preferably in the range of 2:1 to 9:1, and especially preferably in the range of 2:1 to 5:1. It is preferable to use an illumination lamp having a light emitting part provided with a larger number of red light emitting elements than the number of blue light emitting elements, which part gives output beam having a light emission intensity ratio in the above-mentioned range when an appropriate current is applied to the respective red light emitting elements and blue light emitting elements.

The illumination lamp is preferably such that an applied electrical current can be exactly adjusted and the ratio of light emission intensity of red light to that of blue light can be desirably varied depending upon the particular kind of plant by precisely adjusting the electrical current.

If the ratio of light emission intensity of red light to that of blue light is smaller than the above-specified range, i.e., the blue light emission intensity is too large as compared with the red light emission intensity, the desired rate of growth is often difficult to attain. In contrast, if the ratio of red light emission intensity to blue light emission intensity is larger than the above-specified range, i.e., the red light emission intensity is too large, the desired rate of plant growth is also often difficult to attain, and, for example, undesirable growth such as spindly growth or overgrowth tends to occur.

The light irradiation part of the illumination lamp facility as used in the present invention preferably has a mixed light emitting package such that red light emitting elements and blue light emitting elements are arranged in a single light emitting package. The mixed light emitting package preferably has a function such that the red light emitting elements and the blue light emitting elements are capable of being independently controlled.

The ratio of the light emission intensity of red light to the light emission intensity of blue light in the mixed light emitting package is preferably at least 1:1, more preferably in the range of 2:1 to 9:1, and especially preferably in the range of 2:1 to 5:1. By providing the light irradiation part with such mixed light emitting package, the red light emitting elements and the blue light emitting elements can be arranged with enhanced density in the light irradiation part.

Conventional red light emitting elements 2 and blue light emitting elements 3 can be used. For example, light emitting diode (LED) in which the desired wavelength can be easily selected and light energy within the effective wavelength region occupies a predominant part can be used. Laser diode (LD) and a electroluminescent (EL) element can also be used. The EL element used may be either an organic EL element or inorganic EL element.

Red light emitted from the red light emitting elements 2 has a wavelength in the range of 570 nm to 730 nm. Preferably the red light has a center emission wavelength within the range of 640 nm to 680 nm, and a wavelength in the range of the center emission wavelength±50 nm, more preferably the center emission wavelength±30 nm, and especially preferably the center emission wavelength±10 nm.

Blue light emitted from the blue light emitting elements 3 has a wavelength in the range of 400 nm to 515 nm. Preferably the blue light has a center emission wavelength within the range of 400 nm to 515 nm, more preferably 450 nm. The blue light preferably has a wavelength in the range of the center emission wavelength 450±30 nm, more preferably the center emission wavelength 450±20 nm, and especially preferably the center emission wavelength 450±10 nm.

The light emission intensity ratios of individual red light emitting elements and individual blue light emitting elements are not particularly limited, but, the total light emission intensity ratio of plural red light emitting elements and the total blue light emission intensity ratio of plural blue light emitting elements are preferably within the above-mentioned range.

By the term "light emission intensity ratio" as used in the specification, we mean those which are expressed by photosynthetic photon flux density (PPFD; in $\mu mol/m^2$ s).

The red light and the blue light, irradiated from the light irradiation part 11, preferably exhibit a photosynthetic photon flux density in the range of approximately 1 to 1,000 $\mu mol/m^2$ s, more preferably approximately 10 to 500 $\mu mol/m^2$ s and especially preferably approximately 50 to 250 $\mu mol/m^2$ s.

Illumination lamp facilities as preferably used for the plant cultivation are equipped with a control part. Emission intensities of red light and blue light, emitted from the irradiation part 11, can be controlled by varying the current value, applied to red light emitting elements 2 and blue light emitting elements 3, by the controlling part.

The plant cultivating illumination lamp 1 as illustrated in FIG. 1 is provided with a pair of electrodes 41 and 42 for red light emitting elements 2 and a pair of electrodes 43 and 44 for blue light emitting elements 3. The plural red light emitting elements 2 are electrically connected by wires (not shown) to the electrodes 41 and 42. The plural blue light emitting elements 3 are electrically connected by wires (not shown) to the electrodes 43 and 44.

The control part equipped in the illumination lamp facility 1 has a function of independently turning on and off the red light emitting elements 2 and the blue light emitting elements 3 by supplying electric current, respectively, via the electrodes 41 and 42 to the red light emitting elements 2 and via electrodes 43 and 44 to the blue light emitting elements 3.

The control part is provided with a lamp controller (i.e., light emission intensity-controlling means), which can turn on and off the red light emitting elements 2 and the blue light emitting elements 3 so that the red light and the blue light are irradiated alternately or concurrently, and for a desired period of time. Thus, the light emission intensity ratio of red light to blue light, irradiated from the light irradiation part 11, can be controlled so as to achieve the desired growth of plants.

The lamp controller used includes, for example, one type which can vary the light emission intensities of the red light emitting elements and the blue light emitting elements 3 by supplying different electric currents to a part or all of the red light emitting elements 2 and/or a part or all of the blue light emitting elements 3, thereby controlling the total emission intensity ratio of red light to blue light, irradiated from the light irradiation part 11; and another type which varies the light emission intensities of the red light emitting elements and the blue light emitting elements 3 by supplying an electric current only to a part of the red light emitting elements 2 and/or a part of the blue light emitting elements 3 to turn on a limited number of light emitting elements, thereby controlling the total emission intensity ratio of red light to blue light, irradiated from the light irradiation part 11.

In the plant cultivation lamp 1, as specifically disclosed in FIG. 1, provided with a light irradiation part 11 having the same number of red light emitting elements and blue light emitting elements, and with a lamp controller, the same electric current can be supplied to all of the red light emitting elements 2 and all of the blue light emitting elements 3, whereby red light and blue light which have the same light emission intensity are irradiated from the light irradiation part 11.

Alternatively, a plant cultivation lamp 1 which is provided with a light irradiation part having the same number of red light emitting elements and blue light emitting elements, but is not provided with a lamp controller can be used in the case when the same electric current is supplied to all of the red light emitting elements 2 and all of the blue light emitting elements 3.

As another operation of the plant cultivation lamp 1, as illustrated in FIG. 1, provided with a light irradiation part having the same number of red light emitting elements and blue light emitting elements, and with a lamp controller, different currents can be supplied to the red light emitting elements 2 and the blue light emitting elements 3 so that the light irradiation part 11 irradiates light with an emission intensity ratio of red light to blue light being 2:1.

Plant Cultivation Method

The method of cultivating a plant according to the present invention will now be explained specifically and more in detail on an embodiment using the illumination lamp 1 as illustrated in FIG. 1.

The plant cultivation method of the present invention comprises a step (A) of irradiating a plant with a red light and a step (B) of irradiating a plant with a blue light, wherein the red light irradiation step (A) and the blue light irradiation step (B) are independently carried out for a predetermined period of time.

By the term "independently" as used herein, we mean that the red light irradiation step (A) and the blue light irradiation step (B) exist separately in the course of plant cultivation.

The procedure of independently carrying out the red light irradiation step (A) and the blue light irradiation step (B) gives a desired plant growth effect, as compared with a plant cultivation procedure wherein red light and blue light are concurrently irradiated. The reason for which the desired enhanced plant growth can be attained by independently carrying out the red light irradiation step (A) and the blue light irradiation step (B), is not clear. But, it is presumed that the photosynthesis process caused by the red light is different from that caused by the blue light due to the fact that chlorophyll exhibits a red light absorption peak distinct from a blue light absorption peak, therefore, when light and blue light are concurrently irradiated, the photosynthesis process by red light and the photosynthesis process by blue light undesirably interfere with each other.

By the term "predetermined period of time" as used herein, we mean an optional length of time within the course of plant cultivation. The maximum length of the predetermined period of time equals to the entire time length of the course of plant cultivation. The minimum length thereof can be voluntarily set provided that the desired plant growth-enhancing effect can be attained. The predetermined period of time can be expressed in unit of hour, day or minute depending upon the particular length of time.

Each of the red light irradiation step (A) and the blue light irradiation step (B) is carried out independently at least once, preferably at least two times, for the predetermined period of time. In the case when the red light irradiation step (A) and the blue light irradiation step (B) are carried out dividedly in two times or more, time length of each operation of the red light irradiation step (A) and time length of each operation of the blue light irradiation step (B) is preferably at least 1 hour, more preferably in the range of 1 to 48 hours, and especially preferably in the range of 3 to 24 hours.

The red light irradiation step (A) and the blue light irradiation step (B) can be carried out either alternately and continuously, or intermittently with interposition of an operation of concurrently irradiating plant with red light and blue light between each operation of the red light irradiation step (A) and each operation of the blue light irradiation step (B), or with pause of irradiation between each operation of the red light irradiation step (A) and each operation of the blue light irradiation step (B).

Transfer between operation of red light irradiation step (A) and operation of red light irradiation step (A) can be conducted either instantaneously or over a certain length of time. The transfer may be conducted in stages. During the transfer, operation of red light irradiation step (A) and operation of red light irradiation step (A) may overlap with each other, or a pause of irradiation may intervene between operation of red light irradiation step (A) and operation of red light irradiation step (A).

Alternate flashing of red light irradiation and blue light irradiation by quickly repeating light flashing with a high frequency such as 1 Hz or higher is excluded from the light irradiation procedure adopted for independently carrying out the red light irradiation step (A) and the blue light irradiation step (B) for a predetermined period of time in the plant cultivation method of the present invention.

In the alternate flashing of red light irradiation and blue light irradiation by quickly repeating light flashing with a high frequency such as 1 Hz or higher, the photosynthesis reaction and related reactions do not occur to the desired extent. This is because each flashing of red light irradiation and blue light irradiation occurs for a very short length of time which is insufficient for achieving the plant growth effect. The plant growth effect achieved by the alternate flashing is similar to that achieved by the operation of concurrently irradiating plant with red light and blue light.

The plant cultivation method of the present invention can be adopted for any period of time within the entire course of plant cultivation spanning from immediately after the germination of seeds or immediately after the plantation to the harvest.

The plants to be cultivated in the method of the present invention are not particularly limited, and this term means plants in a broad sense which include leaf plants, water plants, root plants, fruit plants, pluses, grains, seeds, algae, house plants, mosses and vegetable planktons.

The procedure of independently carrying out the red light irradiation step (A) and the blue light irradiation step (B) using the above-mentioned illumination lamp facility gives a desired plant growth effect.

An illumination lamp facility equipped with a control part having a lamp controller (i.e., light emission intensity-controlling means) in the irradiation part having red light emitting elements and blue light emitting elements is preferably used for this procedure. Emission intensities of red light to blue light, emitted from the red light emitting elements and the blue light emitting elements, can be desirably controlled for the particular kinds of plants by varying the current value, applied to the red light emitting elements and the blue light emitting elements, by the controlling part.

The control part has a function of independently turning on and off the red light emitting elements and the blue light emitting elements, the red light irradiation and the blue light irradiation can be separately or concurrently carried out, and the irradiation time can be varied so as to attain the desired pint growth promotion effect.

The illumination lamp facility equipped with a control part in the irradiation part having red light emitting elements and blue light emitting elements is also advantageous as compared with the conventional illumination lamp facility having red light emitting means and blue light emitting means which are separately arranged, because the light emitting means can be easily and steadily arranged in the illumination lamp facility and undesirable deviation of the irradiation directions of red light and blue light can be minimized.

The light irradiation part as illustrated in FIG. 1 has a rectangular shape in a plan view, therefore, the illumination lamp facility can be easily set in the position in which a conventional illumination facility such as straight tube fluorescent lamp is set.

The illumination lamp facility is preferably provided with a converter, built in the lamp, of converting alternating current to direct current for LED because of ease in setting and effective utilization of space. The terminal on one side and the terminal on the other side are preferably utilized separately for the red light emission and blue light emission in view of arrangement of electrical sources built therein and dispersion in generation of heat.

Further the illumination lamp facility is preferably provided with a dimmer for controlling LED in plural lamps and desirably adjusting the light emission intensity ratio.

The plant cultivation method of the present invention should not be construed to be limited to the modes mentioned above.

The illumination lamp facility described above is equipped with a lamp controlling means for controlling light emission intensity. The plant cultivation can also be carried out using an illumination lamp facility not equipped with the lamp controlling means. This illumination lamp facility is advantageous in that a lamp controlling means and its accessories can be omitted and the cost of equipment production is reduced.

EXAMPLES

Preparation of Plants to be Tested

In the following examples and comparative examples, leaf lettuce (variety: summer serge) was tested for observing the growth state.

Six seeds of leaf lettuce were shown at equal intervals in each test group on a peat van culture medium, and irradiated with fluorescent light for 12 hours of light per day to be thereby germinated. The seeds were placed under the same irradiation conditions over a period of three days spanning from seeding to germination. Thereafter seedlings were raised under irradiation with fluorescent light to give leaf lettuces for test.

Example 1

The raised seedlings of leaf lettuces for test were placed in an environment control room wherein temperature-, humidity- and carbon dioxide concentration-controlling means were provided. The test leaf lettuces were cultivated for 24 days under conditions of: atmosphere temperature of 22° C. to 25° C.; and humidity of 60% RH, while the leaf lettuces were irradiated with red light and blue light as follows.

An illumination lamp for plant cultivation used had a light emitting part provided with 180 red light emitting elements and 60 blue light emitting elements. Each red light emitting element was comprised of a LED emitting red light having a center wavelength of 660 nm and a wavelength region of 640-680 nm, and each blue light emitting element was comprised of LED emitting blue light having a center wavelength of 450 nm and a wavelength region of 430-470 nm. The illumination lamp further had a control part for controlling the light emitting part so that the red light emitting elements and blue light emitting elements are independently turned on and off.

The red light emitting elements exhibited a total emission intensity, i.e., a total photosynthetic photon flux density (PPFD), of 150 µmol/m²·s. The blue light emitting elements exhibited a total emission intensity, i.e., a total photosynthetic photon flux density (PPFD), of 50 µmol/m²·s. Thus the total emission intensity ratio of red light to blue light was 3:1.

The red light-irradiation step and the blue light irradiation step were alternately and repeatedly carried out for 12 hours for each irradiation time per day, i.e., each light irradiation step was carried out separately and continuously over a period of 12 hours per day. There was no time for which the light irradiation was ceased.

When 24 days elapsed, the light irradiation was stopped and grown leaf lettuces were harvested.

Nutritious liquids applied were prepared and used at the blue light irradiation step and the red irradiation step. The nutritious liquid applied at the blue light irradiation step contained 12 me/L of nitrogen, 4 me/L of phosphorus, 8 me/L of potassium, 4 me/L of calcium, 2 me/L of magnesium and trace amounts of iron. pH of the nutritious liquid was adjusted to 4.5. Temperature of the nutritious liquid was maintained at 15° C.

The nutritious liquid applied at the red light irradiation step contained 25 me/L of nitrogen, 7 me/L of phosphorus, 14 me/L of potassium, 4 me/L of calcium, 2 me/L of magnesium and trace amounts of iron. pH of the nutritious liquid was adjusted to 6. Temperature of the nutritious liquid was maintained at 20° C.

After 24 days cultivation, grown leaf lettuces were harvested. Fresh weight (g) of above-ground part of the leaf lettuces was measured. The inorganic ion ingredients were analyzed to determine the concentrations of nitrate ion, potassium and magnesium per 100 g of fresh weight of above-ground part of the leaf lettuces.

The cultivation results are shown in Table 1. In the examples and the comparative examples, shown in Table 1, the cultivation results are expressed by relative indexes as the values obtained in Comparative Example 1 being 100.

TABLE 1

| Cultivation results*² | Examples, Comparative Examples | | | | | |
|---|---|---|---|---|---|---|
| | Ex. 1 | Ex. 2 | Ex. 3 | Ex. 4 | Ref. Ex. 1 | Co. Ex. 1*¹ |
| Fresh weight of above-ground part | 110 | 105 | 106 | 120 | 100 | 55 |
| Contents per 100 g of fresh weight of above-ground part | | | | | | |
| $NO_3^-$ | 91 | 92 | 94 | 80 | 100 | 109 |
| Potassium | 115 | 105 | 110 | 126 | 100 | 97 |
| Magnesium | 122 | 110 | 105 | 128 | 100 | 92 |

Note;
*¹In Comparative Example 1, red light and blue light were concurrently irradiated
*²Relative indexes as values in Reference Example 1 being 100

Example 2

By the same procedures as described in Example 1, leaf lettuces were cultivated except that pH value of the two kinds of liquid fertilizers (aqueous nutrient solutions) was adjusted to 6 with all other cultivation conditions remained substantially the same as in Example 1. The cultivation results are shown in Table 1.

Example 3

By the same procedures as described in Example 1, leaf lettuces were cultivated except that temperature of the two kinds of liquid fertilizers (aqueous nutrient solutions) was maintained at 20° C. with all other cultivation conditions remained substantially the same as in Example 1. The cultivation results are shown in Table 1.

Example 4

By the same procedures as described in Example 1, leaf lettuces were cultivated except that the nutritious liquids applied at the blue light irradiation step and the red irradiation step were changed as follows. The nutritious liquid applied at the blue light irradiation step contained 12 me/L of nitrogen, 2 me/L of phosphorus, 4 me/L of potassium, 4 me/L of calcium, 2 me/L of magnesium and trace amounts of iron. The nutritious liquid applied at the red light irradiation step contained 18 me/L of nitrogen, 4 me/L of phosphorus, 8 me/L of potassium, 4 me/L of calcium, 2 me/L of magnesium and trace amounts of iron. All other cultivation conditions remained substantially the same as in Example 1. The cultivation results are shown in Table 1.

Reference Example 1

By the same procedures as described in Example 1, leaf lettuces were cultivated except that the same nutritious liquid as used at the red irradiation step was used at both of the blue light irradiation step and the red light irradiation step. All other cultivation conditions remained substantially the same as in Example 1. The cultivation results are shown in Table 1.

Comparative Example 1

By the same procedures as described in Example 1, leaf lettuces were cultivated except that the red light irradiation step and the red light irradiation step were concurrently and continuously carried out for 12 hours per day; and the lamp was left put out for 12 hours per day. The concurrent irradiation of red light and blue light, and the lamp leaving put out were repeated for 24 days. The same nutritious liquid as used at the red light irradiation step in Example 1 was applied at the concurrent irradiation step of blue light and red light, and the same nutritious liquid as used at the blue light irradiation step in Example 1 was applied while the lamp was left put out. All other cultivation conditions remained substantially the same as in Example 1. The cultivation results are shown in Table 1.

As seen from Table 1, when the amounts of nitrogen, phosphorus and potassium as fertilizer ingredients contained in the nutritious liquid applied at the blue light irradiation step (B) are smaller than the amounts of nitrogen, phosphorus and potassium as fertilizer ingredients, respectively, contained in the nutritious liquid applied at the red light irradiation step (A) (Examples 1-4), the following benefits are attained. The content of nitrate ion is smaller than that in Reference Example 1 and Comparative Example 1. Therefore, the lettuces in the examples of the present invention are less bitter tasting and milder than those in the reference example and comparative example. Further, the contents of minerals such as potassium and magnesium are large in the lettuces in the examples of the present invention, and thus, the lettuces have an enhanced nutritious value and mild taste, and a high added value. In contrast, the lettuces in Reference Example 1 and Comparative Example 1 are poor in the mildness of taste and in the nutritious value.

The invention claimed is:

1. A method of cultivating a plant comprising a step (A) of irradiating a plant with a red light and a step (B) of irradiating the plant with a blue light, wherein the red light irradiating step (A) and the blue light irradiating step (B) are independently carried out for a predetermined period of time under cultivation conditions such that amounts of nitrogen, phosphorus and potassium as fertilizer ingredients applied at the blue light irradiating step (B) are smaller than amounts of nitrogen, phosphorus and potassium as fertilizer ingredients, respectively, applied at the red light irradiating step (A).

2. The method of cultivating a plant according to claim 1, wherein the fertilizer ingredients are applied in amounts such that a growth medium at the blue light irradiating step (B) contains 10 to 15 milliequivalents/L(me/L) of nitrogen, 1 to 4 me/L of phosphorus and 2 to 6 me/L of potassium, and a growth medium at the red light irradiating step (A) contains 15 to 20 me/L of nitrogen, 3 to 6 me/L of phosphorus and 6 to 9 me/L of potassium.

3. The method of cultivating a plant according to claim 1, wherein the fertilizer ingredients are applied in a form of a nutritious liquid at each of the blue light irradiating step (B) and the red light irradiating step (A), and the nutritious liquid applied at the blue light irradiating step (B) has a pH value smaller than a pH value of the nutritious liquid applied at the red light irradiating step (A).

4. The method of cultivating a plant according to claim 1, wherein the fertilizer ingredients are applied in a form of a nutritious liquid at each of the blue light irradiating step (B) and the red light irradiating step (A), and the nutritious liquid applied at the blue light irradiating step (B) has a pH value in a range of 4 to 5, and the nutritious liquid applied at the red light irradiating step (A) has a pH value in a range of 5 to 6.5.

5. The method of cultivating a plant according to claim 1, wherein the fertilizer ingredients are applied in a form of a nutritious liquid at each of the blue light irradiating step (B) and at the red light irradiating step (A), and a temperature of the nutritious liquid applied at the blue light irradiating step (B) is lower than a temperature of the nutritious liquid applied at the red light irradiating step (A).

6. The method of cultivating a plant according to claim 5, wherein the temperature of the nutritious liquid applied at the blue light irradiating step (B) is in a range of 10° C. to 18° C. and the temperature of the nutritious liquid applied at the red light irradiating step (A) is in a range of 15° C. to 25° C.

7. The method of cultivating a plant according to claim 1, wherein the plant is selected from algae, phytoplankton and euglena.

8. The method of cultivating a plant according to claim 1, wherein the red light irradiating step (A) and the blue light irradiating step (B) are alternately and repeatedly carried out over a period of at least one hour for an irradiation time for each of the red light irradiating step (A) and the blue light irradiating step (B).

9. The method of cultivating a plant according to claim 1, wherein the red light irradiating step (A) and the blue light irradiating step (B) are carried out using an illumination lamp facility having red light emitting elements and blue light emitting elements, both of which are capable of being independently operated, and the red light emitting elements and the blue light emitting elements exhibit a light emission intensity ratio of red light to blue light of at least 1:1 as expressed by a ratio of photosynthetic photon flux density of red light to blue light.

10. The method of cultivating a plant according to claim 1, wherein the red light irradiating step (A) and the blue light irradiating step (B) are carried out using an illumination lamp facility having red light emitting elements and blue light emitting elements, both of which are capable of being independently operated, and the red light emitting elements and the blue light emitting elements exhibit a light emission intensity ratio of red light to blue light in the range of 2:1 to 9:1 as expressed by a ratio of photosynthetic photon flux density of red light to blue light.

* * * * *